(12) United States Patent
Hack et al.

(10) Patent No.: US 6,589,246 B1
(45) Date of Patent: Jul. 8, 2003

(54) METHOD OF APPLYING AN ACTIVE COMPRESSIVE FORCE CONTINUOUSLY ACROSS A FRACTURE

(75) Inventors: Bradford H. Hack, Arcadia, CA (US); Terry M. Mattchen, Santa Barbara, CA (US)

(73) Assignee: Poly-4 Medical, Inc., Goleta, CA (US)

( * ) Notice: Subject to any disclaimer, the term of this patent is extended or adjusted under 35 U.S.C. 154(b) by 0 days.

(21) Appl. No.: 09/844,809

(22) Filed: Apr. 26, 2001

(51) Int. Cl.[7] ............................................. A61B 17/56
(52) U.S. Cl. ....................................................... 606/74
(58) Field of Search .......................... 606/74, 151, 232; 623/13.2, 13.19

(56) References Cited

U.S. PATENT DOCUMENTS

| | | | |
|---|---|---|---|
| 3,841,015 A | 10/1974 | Gregory ......................... 43/44 |
| 3,987,497 A | * 10/1976 | Stoy et al. ................... 427/171 |
| 4,156,574 A | * 5/1979 | Boden ....................... 24/115 M |
| 4,301,551 A | 11/1981 | Dore et al. .......................... 3/1 |
| 4,321,854 A | 3/1982 | Foote et al. ........................ 87/6 |
| 4,731,084 A | 3/1988 | Dunn et al. .................... 623/13 |
| 4,880,002 A | * 11/1989 | MacGregor ................... 521/61 |
| 4,883,486 A | 11/1989 | Kapadia et al. ............... 623/13 |
| 4,917,700 A | 4/1990 | Aikins ........................... 623/13 |
| 4,932,972 A | 6/1990 | Dunn et al. ................... 623/13 |
| 5,318,575 A | 6/1994 | Chesterfield et al. ........ 606/151 |
| 5,356,412 A | * 10/1994 | Golds et al. ................... 24/170 |
| 5,356,417 A | * 10/1994 | Golds ....................... 24/16 PB |
| 5,383,905 A | * 1/1995 | Golds et al. ............. 24/136 L |
| 5,456,722 A | 10/1995 | McLeod et al. .............. 623/13 |
| 5,628,756 A | 5/1997 | Barker, Jr. et al. ......... 606/139 |
| 5,659,994 A | 8/1997 | Cutter et al. .................... 43/44 |
| 5,725,582 A | 3/1998 | Bevan et al. .................. 623/17 |
| 5,852,926 A | 12/1998 | Breedlove .................... 57/210 |
| 5,868,748 A | 2/1999 | Burke .......................... 606/74 |
| 6,132,871 A | 10/2000 | Andrews .................... 428/377 |

* cited by examiner

*Primary Examiner*—Kevin Shaver
*Assistant Examiner*—Melba Bumgarner
(74) *Attorney, Agent, or Firm*—William L. Johnson

(57) ABSTRACT

A method of applying an active compressive force continuously across a fracture by wrapping fractured bone segments in an energy-inducing surgical cable having a predetermined elastic property that stretches about 30 to 100% of its original length. The cable is wrapped around the bone segments, applying an energy-inducing continuous compressive force to the bone segments by elongating while maintaining the bone segments in compression as the bone segments mend.

9 Claims, 4 Drawing Sheets

METHOD OF APPLYING AN ACTIVE COMPRESSIVE FORCE CONTINUOUSLY ACROSS A FRACTURE

BACKGROUND OF THE INVENTION

1. Field of the Invention

The invention relates to surgical repair of fractured body tissues and bones; and, more particularly, to repairing fractures by holding bones or bone fragments together to permit healing.

2. Related Art

At present there are many products known for repairing human body tissues and bones where a repair is required after surgery or an injury. It is well known to use elongated strands as fasteners or staples to apply a compressive force across a fracture or body tissues, bones or bone fragments, after a surgical repair.

In U.S. Pat. No. 5,318,575 to Chesterfield et al., a method of using a surgical repair suture product is disclosed. A similar method using a load-bearing polymer cable is disclosed in U.S. Pat. No. 5,456,722 to McLeod et al. Both patents suggest using a braided tape reinforced with ultra-high molecular weight high-tenacity fibers. Such a product is sold under the trademark "Spectra" manufactured by Allied Signal Corp. This Spectra product has a very high strength, straight pull, and low elongation at break. The data sheet on Spectra™ indicates that it has an elongation at 2.9% to 4.4%. U.S. Pat. No. 4,413,110 directed to this product makes the same claim. Chesterfield et al. states that an elongation below 5% is preferred.

Thus, both prior art patents emphasize that a product having low elongation is desired. U.S. Pat. No. 4,301,551 to Dore et al. also discloses such a cord (referred to in the patent as a "spring". However, the spring is disclosed as having a low modulus of elasticity. In addition, Dore uses a large, hollow, squishy tube made of soft elastomer to get its elasticity and its outer fibers wound over large flanges on the end fittings (for grip). Dore's product works by compressing the soft inner core; there are no outer fibers controlling and limiting the amount of stretch. Dore's product puts high stresses on the outer fibers while returning low working forces. Further, Dore's product is intended as a ligament replacement, not as a suture.

Rubber bands and o-rings of elastomeric material have been proposed for applying such a compressive force. Others have proposed a more stable system using a complex arrangement of metal articulating devices having springs as the active component. Still others have tried composite designs of metal with elastomeric inserts to provide elastic properties. Nevertheless, the largest portion of the surgical community uses rigid metal such as plates and cables since such devices are more secure and stable. The products and methods disclosed in the aforementioned patents are attempts to get away from such rigid and complex devices while providing cables that can provide the compressive forces required to repair fractures and the like.

INVENTION SUMMARY

It is an object of this invention to provide a method of repairing fractures and the like using an energy-inducing surgical cable.

It is still further an object of the invention to provide a method for applying an active compressive force continuously across a fracture or the like.

It is a further object of the invention to carry out the foregoing objects using a surgical cable having a predetermined elastic property that stretches about 30 to 100% of its original length.

These and other objects are preferably accomplished by providing an energy-inducing surgical cable having a predetermined elastic property that stretches about 30 to 100% of its original length and is wrapped around the bone segments applying an energy-inducing continuous compressive force to the bone segments by elongating while maintaining the bone segments in compression as the bone segments mend.

DETAILED DESCRIPTION OF THE PREFERRED EMBODIMENTS

Figure 1:
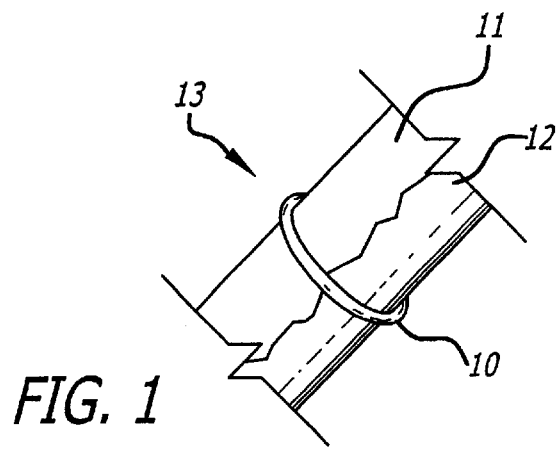
FIG. 1 is a perspective view of a fractured bone having 2 segments wrapped by a cable in accordance with the teachings of the invention.

FIG. 1 shows a loading-bearing energy-inducing surgical cable 10 connecting two small bone fragments 11, 12 of a bone 13 together. Obviously, cable 10 can be used in the repair of any bone fragments, body tissues, etc.

Figure 2:
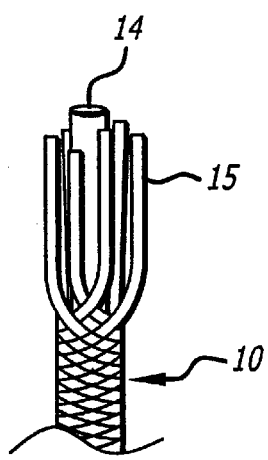
FIG. 2 is a detailed perspective view of a portion of the cable of FIG. 1.
Figure 3:
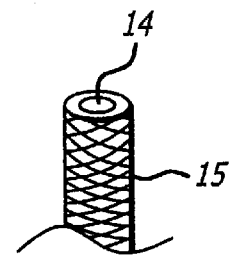
FIG. 3 is a perspective view of the portion of the cable of FIG. 2 in final braided condition.
Figure 4:
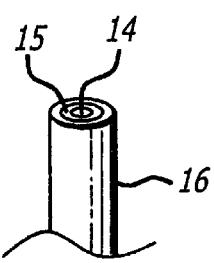
FIG. 4 is a perspective view of a modification of the cable of FIG. 3.

As seen in FIG. 2, cable 10 is formed of a polymer core 14 having a plurality of outer fibers 15 that are braided (see FIG. 3) to form a reinforcing jacket. If desired, as seen in FIG. 4, an outer coating 16 may be applied over braided fibers 15. Core 14 is of a polymeric material, such as nylon, polyester, polyethylene or fluorocarbon, that has been processed by several cycles of stretching and tempering using methods commonly applied today. Multi-core arrangements with different polymers, depending on the mechanical performance desired, may also be used. Although the finished cable 10 has a certain elastic property, core 14 is the primary source and preferably has an elongation of about 50 to 150% of its original length and may have an axial stiffness of about 5 to 20 Newtons (N) per millimeter. Axial stiffness, of course, is dependent on the size of the cable that is selected by the user.

Fibers 15 are fine fibers of a high strength non-stretch material that are braided over an elastic polymer core 14.

Figure 5:
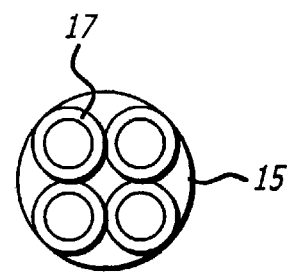
FIG. 5 is an end view of another modification of the cable of FIGS. 3 and 4.

The fiber size and braid density determine the stress-strain results of the final cable. Applicants' cables can be made to stretch 30–100%. For example, one present cable of 1.5 mm diameter has a axial stiffness of 10 N/mm and a stretch-to—failure of 60% over original length. Another cable has a diameter of 0.5 mm with an axial stiffness of 5 N/mm and a stretch-to-failure of 60% over its original length. Although the stretch-to-failure and axial stiffness can be proportional, the mechanical properties can be modified to accommodate the surgical application and instrumentation. If a multi-core 17 is used, as seen in FIG. 5, fibers 15 may be braided about the plurality of cores 17 (otherwise identical to core 14). In both cases, the stretch of the cores 14, 17 is limited creating the relationship of stress-to-strain desired.

Coating 16 (FIG. 4) may be applied to either embodiment of FIGS. 2 and 5 and is preferably of polyethylene, polyester, silicone or any material suitable to protect and/or enhance the performance of cable 10.

It can be seen that we have developed a cable that has the elastic properties required by the body while having the strength necessary of a structural element.

Figure 6:
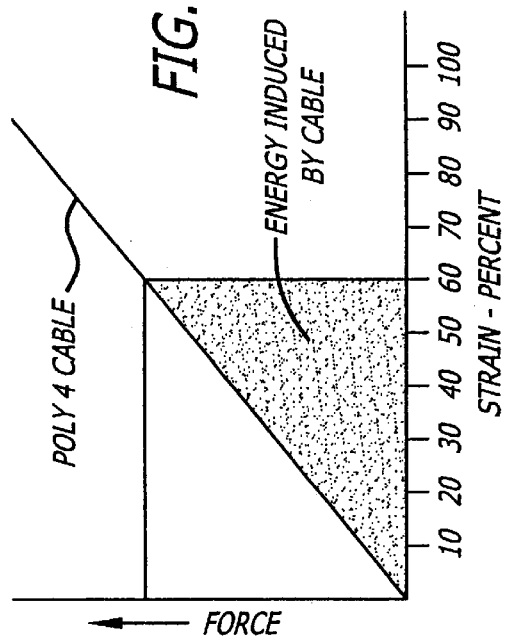
FIG. 6 is a graphical illustration showing force/displacement relationships of cables of different materials.
Figure 7:
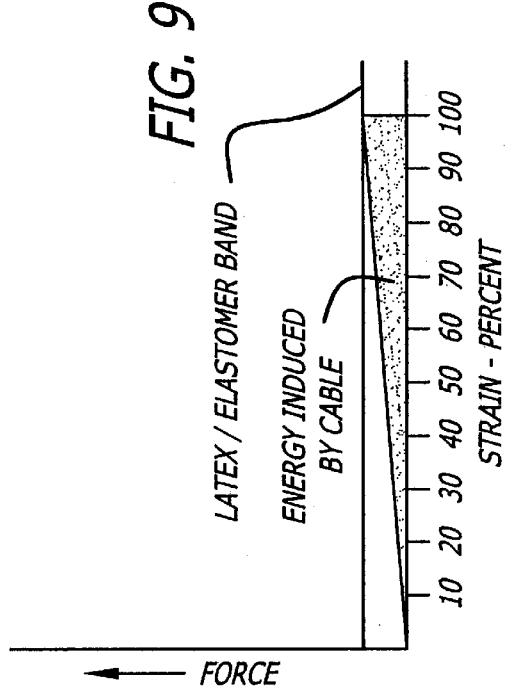
FIGS. 7, 8 and 9 are graphical illustrations of how differences in performance can be achieved by varying the methods of applying different composition cables to a fracture.
Figure 8:
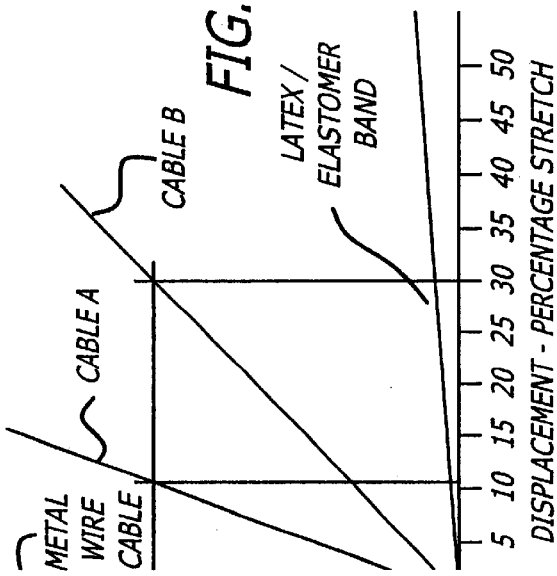
Figure 9:
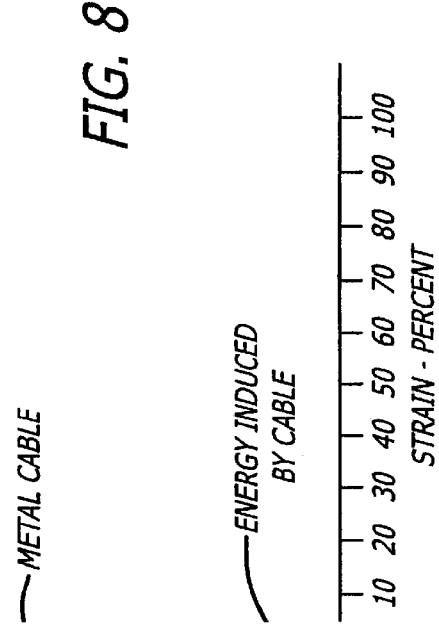

As seen in FIG. 6, the stress/strain relationship of three different cables is shown. Applicant's cable is referred to in FIG. 7 as Poly 4. FIGS. 7, 8 and 9 show the energy imparted into the bone by stretching the cable to a given force and then setting it. The potential energy imparted by the cable is defined as the area under the force-displacement line (hatched pattern in FIGS. 7 to 9). The metal cable (FIG. 8) has only a tiny displacement (stretch) so its ability to store energy is very small. Indeed, in the actual practice of pulling bone surfaces together it is very unlikely that it stretches at all, relying instead on forcefully compressing the bone fragments to obtain a tight joint. In addition, if the bone resorbs only a few hundredths of an inch, the joint will lose that compression and now be loose. FIG. 9 shows the energy of a latex or rubber cable. This cable, although it can be stretched, does not have much strength and therefore cannot develop the forces required to hold the bone fragments in proper position.

FIG. 6 shows the differences in performance that can be achieved by varying the above methods. Cable A and Cable B demonstrate different stress/strain performance depending on how the different core properties, fiber properties and braiding variations are put together.

Cable A is made to have properties that require high strength yet be elastic enough to allow some movement, however limited, of the fixation construct. This capability is very important because once the metal cables in present use are set and there is any repositioning of the construct or bone resorption, the system becomes loose. This is because the metal cable, being rigid, cannot compensate for nor does it allow for any motion.

There are yet other surgical procedures, for example in the spine, where an even more elastic property is required to allow controlled movement of the spinal process. Here the cable can be made with an extra jacket that will provide an upper limit of motion. It can be seen then, that the proper fixation requirement for bone fracture reunion would be for a cable, such as that in FIG. 7, that is capable of generating high compressive force and that is able to maintain its compressive force even though there may be some bone resorption and other inter-fragmentary motion that occurs during normal healing.

It should be pointed out that bone is a living thing; it flexes; it needs to flex as part of its normal physiology. Cables that don't flex (steel or otherwise) and steel plates don't work well for this reason. They fatigue under these conditions and fracture. The elastomeric cable of this invention has a much higher fatigue life, but more importantly, it allows some flexibility while maintaining a continuous active compression across the bone fragments, which promote the healing process.

Figure 10:
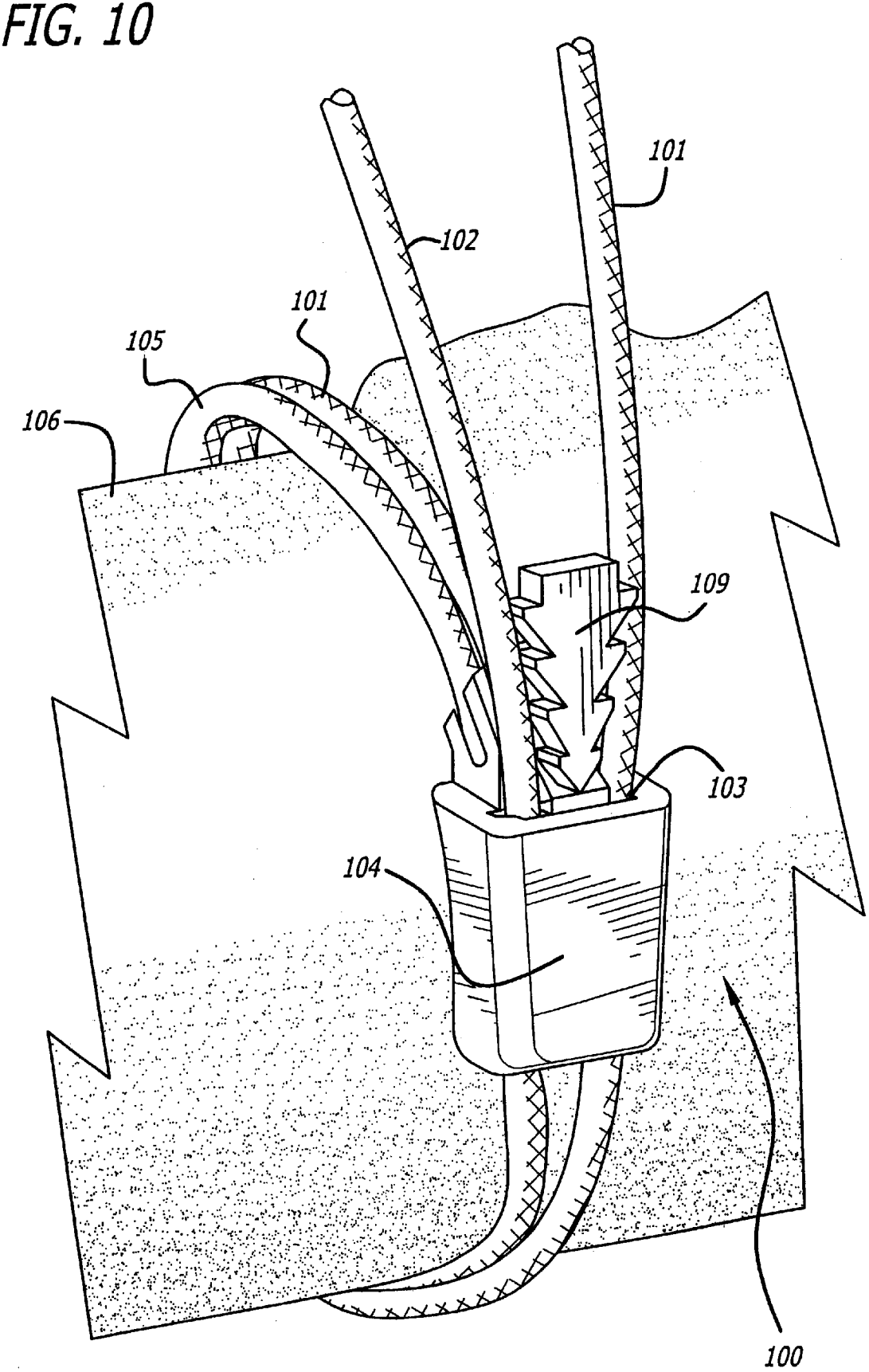
FIG. 10 is a perspective view of cable connecting means used with the cable of our invention.
Figure 11:
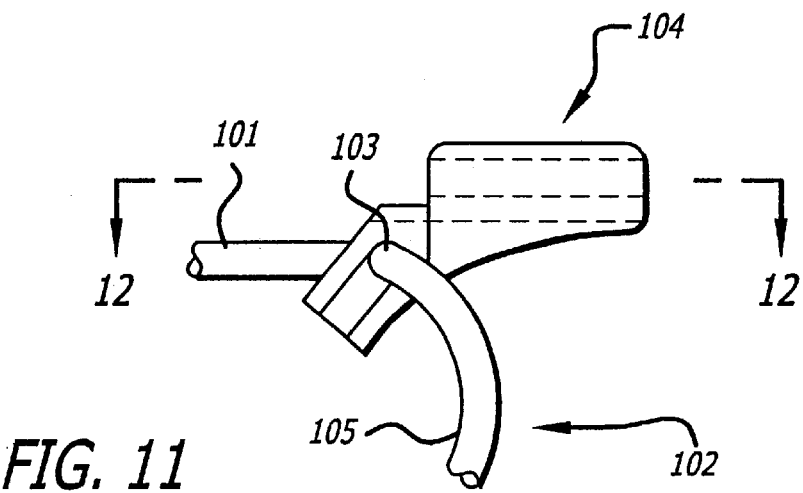
FIG. 11 is a side view of the connector of the connecting means of FIG. 10 illustrating a cable connected thereto.
Figure 12:
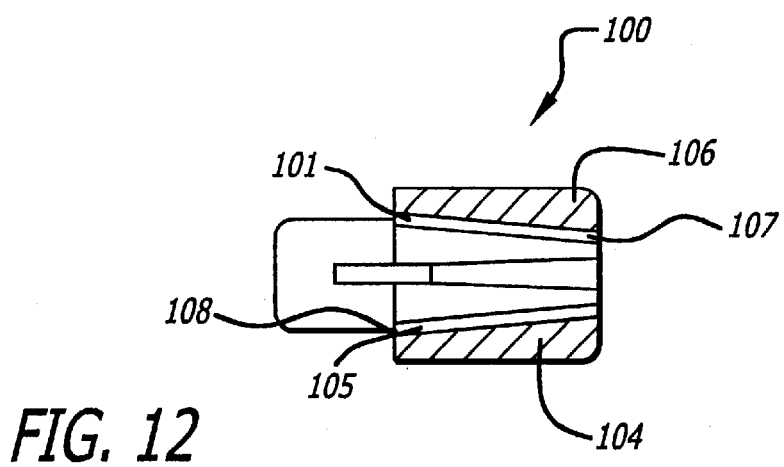
FIG. 12 is a sectional view taken along lines 12—12 of FIG. 11.

Although any suitable means may be used to hold the free ends of the cable together across a fracture or the like during the healing process, one such connecting means 100 is shown in FIG. 10. Here, one of the free ends 101 of cable 102 is passed through a hole 103 in a connector block 104 (see also FIG. 11). The free cable ends (ends 101, 105) are wrapped around the bone segments 106 and pass through block 104. As can be seen in FIG. 12, block 104 has a trapezoidally-shaped inner chamber 106 so that ends 101, 105 extend from the smaller end 107 to the wider end 108 of chamber 106.

Figure 13:
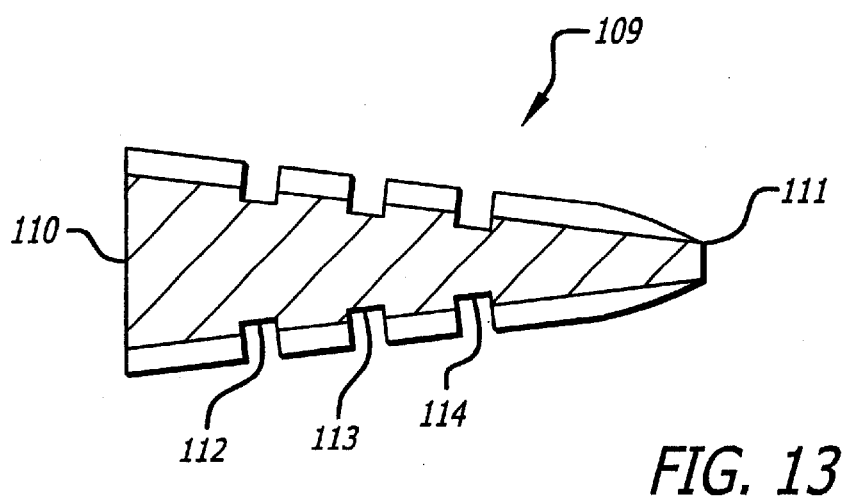
FIG. 13 is a top plan view of one of the components of the connecting means of FIG. 10.

As seen in FIG. 13, a wedge 109 is provided generally triangular in cross-section, thus having a wider end 110 tapering to a pointed end 111. A plurality of spaced grooves, such as grooves 112 through 114 are provided along wedge 109 on each side thereof.

As seen in FIG. 10, wedge 109 is pushed into chamber 106 of block 104 forcing cable ends 101, 105 against the inner wall of the chamber 106. This locks the cable 102 in block 104. At some point during the wedging process, wedge 109 floats between the cable ends 101, 105 to compensate for one end of the cable being slightly lesser in diameter than the other. The grooves 112 through 114, and the triangular configuration of wedge 109 serve to put tension on cable ends 101, 105 if pulling of the cable 102 out of block 104 takes place.

There is thus described a connecting means 100 for cable 102 which serves to lock the cable ends 101, 105 together during the healing process.

Applicants' cables may be set at loads of 400 to 800 N, depending on the surgical application. These forces are necessary for the cable to be effective. However, the cable must also allow for some movement. The cables in the prior art patents, where they are simply tied off or the ends anchored with screws, apply a modest preload and are not effective. The knots slip easily in the prior art cables, making them quite unreliable. Applicants' cable also has advantages over metal cable in its elastic properties, while its distinction over the latex and o-ring elastomers is its strength by many orders of magnitude.

Applicants' cable is designed to deliver a force/displacement (energy) component into the fixation construct of the surgeon to meet the physiological needs of the body and the fixation needs of the surgeon. This is in opposition to the devices in the prior art patents that actually emphasize the stiffness or non-stretch properties and thus teach away from Applicants' invention.

Thus, there is disclosed a cable having a diameter of about 1.5 mm that may have an axial stiffness of 5–25 N/mm and which can be set at loads of about 400 to 800 N to provide a continuous active compressive force across a fracture or the like.

The invention includes a method for applying a continuous active compressive force across a pair of mating fractured bone segments by wrapping the segments in a cable having a predetermined elastic property that stretches about 30 to 100 percent of its original length while maintaining an active compressive force on the bone segments as they mend. The cable preferably has at least one central core of a polymer material with an outer braided cover of a fiber material. Preferably, the method includes the step of wrapping the segments in a cable having a predetermined elastic property that stretches about 60 percent of its original length. Most preferably the cable has a pair of free ends and the method includes a step of locking the cable ends on a fixed firm position about the bone segments.

Although a particular embodiment of the invention is disclosed, variations thereof may occur to an artisan, and the scope of the invention should only be limited by the scope of the appended claims.

We claim:

1. A method of repairing a bone fracture having at least two mating bone segments, comprising the steps of:

providing an elastomeric cable having an original length and a predetermined elastic property;

storing mechanical energy in said elastomeric cable by pre-tensioning said elastomeric cable to a predetermined working tension while stretching said cable to a working length which is longer than said original length;

applying a compressive force across the fracture by fixing said stretched and pre-tensioned elastomeric cable across the mating bone segments with said working tension tending to compress the fracture; and maintaining a continuous active compression across the fracture during bone healing while allowing normal bone resorption and bone motion, by delivering stored mechanical energy from said elastomeric cable to the bone.

2. The method of claim 1 wherein said predetermined elastic property is an axial stiffness in the range 5–25 Newtons per millimeter of elongation.

3. The method of claim 2 wherein said predetermined working tension is in the range of 400–800 Newtons.

4. The method of claim 3 wherein said working length is at least 30 percent longer than said original length.

5. The method of claim 4 wherein said working length is in the range 30–100 percent longer than said original length.

6. The method of claim 5 wherein said working length is approximately 60 percent longer than said original length.

7. The method of claim 1 wherein said pre-tensioned and stretched elastomeric cable has free ends;

and wherein said pre-tensioned and stretched elastomeric cable is fixed by wrapping said cable around the fracture then securing the free ends with a cable locking device.

8. The method of claim 1 wherein said cable is comprised of a central core of a polymer material having a plurality of braided outer fibers surrounding said central core.

9. The method of claim 8 wherein said fibers are of a high strength, low stretch protective material.

* * * * *